United States Patent [19]

Behr et al.

[11] Patent Number: 5,530,164
[45] Date of Patent: Jun. 25, 1996

[54] PROCESS FOR THE PRODUCTION OF TRANS-3,3,5-TRIMETHYLCYCLOHEXYL ETHYL ETHER

[75] Inventors: Arno Behr, Duesseldorf; Christoph Lohr, Dortmund; Hans-Peter Handwerk, Duesseldorf; Thomas Gerke, Neuss, all of Germany

[73] Assignee: Henkel Kommanditgesellschaft auf Aktien, Duesseldorf, Germany

[21] Appl. No.: 398,392

[22] Filed: Mar. 3, 1995

Related U.S. Application Data

[63] Continuation of Ser. No. 30,152, May 17, 1993, abandoned.

[30] Foreign Application Priority Data

Sep. 17, 1990 [DE] Germany ............... 40 29 425.0

[51] Int. Cl.[6] .................................................. C07C 41/01
[52] U.S. Cl. ......................................................... 568/579
[58] Field of Search ............................................... 568/579

[56] References Cited

U.S. PATENT DOCUMENTS 4,130,509 12/1978 Conrad et al. .

FOREIGN PATENT DOCUMENTS 2661006 6/1978 Germany .
2658567 6/1978 Germany .

OTHER PUBLICATIONS

Bulletin of the Chemical Society of Japan, vol. 51, No. 11, 1978, Shigeo Nishimura et al.: "Hydrogenation and Hydrogenolysis. XVI. The Reactions of Two Isomeric Enol Ethers of e–Methylcyclohexanone over Platinum Group Metals", see p. 3330—p. 3334.

Bulletin of the Chemical Society of Japan, vol. 44, 1971 Shigeo Nishimura et al.: "Hydrogenation and Hydrogenolysis. XIII. The Hydrogenation of Ethyl 4–Methyl–1–cyclohexenyl Ether over Platinum Metal Catalysts", see p. 166—p. 172.

J. Org. Chem., vol. 35, No. 8, 1970, Ernest L. Eliel et al.: "Reductions with Metal–Ammonia Combinations. II. Monothioacetals and Monothioketals. A Synthesis of Alkoxy Mercaptans", see p. 2716—p. 2722.

J. Mol. Catal. 1985 (29) 41).

Primary Examiner—Johann Richter
Assistant Examiner—John Peabody
Attorney, Agent, or Firm—Wayne C. Jaeschke; John E. Drach; Henry E. Millson, Jr.

[57] ABSTRACT

Process for the highly stereoselective production of trans-3,3 5-trimethylcyclohexyl ethyl ether which comprises contacting 3,3,5-trimethycyclohexenyl ethyl ether with hydrogen in the presence of an effective amount of a palladium catalyst at from about 20° C. to about 100° C. and from about 1 to about 10 bar hydrogen pressure

12 Claims, No Drawings

PROCESS FOR THE PRODUCTION OF TRANS-3,3,5-TRIMETHYLCYCLOHEXYL ETHYL ETHER

This application is a continuation of application Ser. No. 08/030,152, filed on May 17, 1993, now abandoned.

BACKGROUND OF THE INVENTION

1. Field of the Invention

The invention relates to an improved process for the production of the fragrance trans-3,3,5-trimethylcyclohexyl ethyl ether by hydrogenation of the enol ether 3,3,5-trimethylcyclohexenyl ethyl ether in a high yield and with high selectivity under particularly mild reaction conditions.

2. Statement of Related Art

The hydrogenation of enol ethers is basically known from the literature. For example, A. Yanagawa, Y. Suzuki, I. Anazawa, Y. Takagi and S. Yada hydrogenated methyl-4-tert.butyl- 1-cyclohexenyl ether. They obtained mainly the cis-isomer when the catalyst contained metallic rhodium and mainly the trans-isomer when the catalyst contained a rhodium complex (J. Mol. Catal. 1985 (29) 41).

S. Nishimura, M. Katagiri, T. Watanabe and M. Uramoto have shown that the Pd-catalyzed hydrogenation of the enol ethers of 2- and 4-methyl cyclohexanone leads with high stereoselectivity to the saturated cis-ethers (Bull. Chem. Soc. Jpn. 1971 (44) 166).

In another work, S. Nishimura, K. Kagawa and N. Sato (Bull. Chem. Soc. Jpn. 1978 (51) 3330) showed that, in Pd-catalyzed hydrogenation in ethanol, the corresponding isomeric enol ethers of 3-methyl cyclohexanone, 1-ethoxy-3-methyl and 1-ethoxy-5-methyl cyclohexene lead mainly to the trans-ethers in the initial phase of the reaction. However, the cis components were still 23% and 15%. In addition, the reaction has the disadvantage that it has to be carried out in a solvent. On the one hand, this unnecessarily complicates working up of the product; on the other hand, it can give rise to the formation of secondary products.

According to the teaching of DE 26 61 006 C2, 3,3,5-trimethylcyclohexyl ethyl ether (1) can be obtained in a yield of 75% of the theoretical by nickel-catalyzed hydrogenation of 3,3,5-trimethylcyclohexenyl ethyl ether ("enol ether"). The required trans-form of the ether is formed with 95% selectivity. However, energy-intensive temperature and pressure conditions are required for this reaction. According to the claims of the document in question, the reaction is carried out*at temperatures of 150° to 200° C. and under hydrogen pressures of 10 to 200 bar.

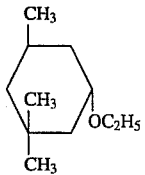

(1)

In order to reduce energy consumption and the potential dangers involved in handling hydrogen gas under such conditions and to increase the life of the reactors, a search was made for a process to produce (1) which could be carried out under much milder conditions for at least the same selectivity. In addition, for reasons of economy, the yield obtained from the hydrogenation of the enol ether would be improved for low concentrations of catalyst. Finally, the process would be carried out under conditions which made the presence of a solvent unnecessary.

DESCRIPTION OF THE INVENTION

According to the invention, these objectives have been achieved by a process for the production of trans-3,3,5-trimethylcyclohexyl ethyl ether with only small contents of cis-ether, characterized in that 3,3,5-trimethylcyclohexenyl ethyl ether is hydrogenated in the presence of palladium catalysts at 20° to 100° C./1 to 10 bar hydrogen pressure without using a solvent and the hydrogenation product is worked up in the usual way.

A preferred embodiment of the invention is characterized in that palladium on carbon is used as the catalyst.

In a particularly preferred embodiment, the hydrogenation is carried out at 20° to 50° C.

Another preferred embodiment of the present invention is characterized in that the hydrogenation is carried out under hydrogen pressures of 1 to 6 bar.

The hydrogenation of the 3,3,5-trimethylcyclohexenyl ethyl ether by the process according to the invention may be carried out with very low concentrations of catalyst. Accordingly, another preferred embodiment of the invention is characterized in that the molar ratio of palladium and 3,3,5-trimethyl cyclohexenyl ethyl ether is 1:1000 to 1:15000 and preferably 1:1000 to 1:5000.

The process according to the invention also has the advantage that the catalyst can be filtered off very easily and may be repeatedly reused without any significant loss of activity and without any losses of yield or stereoselectivity.

Hydrogenation under the conditions of the process according to the invention represents an improvement over the prior art in the following respects:

it is quantitative, the desired trans form of the 3,3,5-trimethylcyclohexyl ethyl ether is formed with selectivities of 97 to 98%, it takes place at far lower temperatures, it takes place under far lower pressures, it does not require a solvent, it takes place at very low catalyst concentrations, the catalyst may be repeatedly reused without any loss of yield or stereoselectivity.

The following Examples are intended to illustrate the invention without limiting it in any way.

EXAMPLES 3,3,5-Trimethylcyclohexenyl ethyl ether ("enol ether") was prepared in accordance with DE 26 61 006 C2 from 3,3,5-trimethyl cyclohexanone and orthoformic acid triethyl ester in the presence of a little p-toluenesulfonic acid.

COMPARISON EXAMPLE 1 (DE 26 61 006 C2)

Reaction: 18.4 g catalyst (Girdler Nickel 49A®) were added to 252 g (1.5 mol) enol ether, followed by slow heating to 200° C. in an autoclave under 50 bar hydrogen pressure. The mixture was then left to react for one hour under a hydrogen pressure of 180 bar.

Working up: The mixture was cooled, the product was decanted off from the catalyst and subsequently fractionated in vacuo.

Yield: 184 g 3,3,5-trimethylcyclohexyl ethyl ether (74% of the theoretical).

Purity: 95% trans-3,3,5-trimethylcyclohexyl ethyl ether
5% cis-3,3,5-trimethylcyclohexyl ethyl ether

EXAMPLE 1

Reaction: 252 g (1.5 mol) enol ether were introduced into a laboratory autoclave equipped with a turbine stirrer and 2.4 g (1.1 mmol Pd) catalyst (5% palladium on active carbon) were then added. The autoclave was then placed under a hydrogen pressure of 6 bar and the reaction was started. In the course of the exothermic reaction, the temperature of the reaction mixture rose from 25° to 50° C. After 60 minutes, the yield of trans-3,3,5-trimethylcyclohexyl ethyl ether amounted to 90%. The reaction mixture was then stirred for another 40 minutes at 100° C. under constant hydrogen pressure.

Working up: as in Comparison Example 1

Yield: 250 g 3,3,5-trimethylcyclohexyl ethyl ether (quantitative)

Purity: 98% trans-3,3,5-trimethylcyclohexyl ethyl ether
2% cis-3,3,5-trimethylcyclohexyl ethyl ether

EXAMPLE 2

Reaction: As Example 1, but under a constant hydrogen pressure of 2 (not 6) bar and with stirring for 70 (not 40) minutes.

Working up: as in Example 1.

Yield: 250 g 3,3,5-trimethylcyclohexyl ethyl ether (quantitative)

Purity: 97% trans-3,3,5-trimethylcyclohexyl ethyl ether
3% cis-3,3,5-trimethylcyclohexyl ethyl ether

EXAMPLE 3

Reaction: As Example 1, but under a constant hydrogen pressure of 4 (not 6) bar and with stirring for 50 (not 40) minutes.

Working up: as in Example 1.

Yield: 250 g 3,3,5-trimethylcyclohexyl ethyl ether (quantitative)

Purity: 97% trans-3,3,5-trimethylcyclohexyl ethyl ether
3% cis-3,3,5-trimethylcyclohexyl ethyl ether

EXAMPLE 4

Reaction: As Example 1, but with 0.2 18 g catalyst (0.1 mmo 1 Pd).

Working up: as in Example 1.

Yield: 250 g 3,3,5-trimethylcyclohexyl ethyl ether (quantitative)

Purity:. 97% trans-3,3,5-trimethylcyclohexyl ethyl ether
3% cis-3,3,5-trimethylcyclohexyl ethyl ether

EXAMPLE 5

Reaction: As Example 1, but using a catalyst which had already been used 14 times under the same reaction conditions.

Working up: as in Example 1.

Yield: 250 g 3,3,5-trimethylcyclohexyl ethyl ether (quantitative)

Purity:. 97% trans-3,3,5-trimethylcyclohexyl ethyl ether
3% cis-3,3,5-trimethylcyclohexyl ethyl ether

What is claimed is:

1. A process for the highly stereoselective production of trans-3,3,5-trimethylcyclohexyl ethyl ether which comprises contacting 3,3,5-trimethycyclohexenyl ethyl ether with hydrogen in the presence of an effective amount of a catalyst consisting essentially of palladium at from about 20° C. to about 100° C. and from about 1 to about 10 bar hydrogen pressure.

2. The process of claim 1 wherein said catalyst is palladium on carbon.

3. The process of claim 1 wherein said process is carried out at a temperature of from about 20° C. to about 50° C.

4. The process of claim 1 wherein said process is carried out under a hydrogen pressure of from about 1 to about 6 bar.

5. The process of claim 1 wherein the molar ratio of said palladium catalyst to 3,3,5-trimethylcyclohexenyl ethyl ether is from about 1:1000 to about 1:15000.

6. The process of claim 5 wherein said molar ratio is from about 1:1000 to about 1:5000.

7. The process of claim 1 wherein said temperature is in the range of from about 20° C. to about 50° C., and the hydrogen pressure is from about 1 to about 6 bar.

8. The process of claim 7 wherein the molar ratio of said palladium catalyst to 3,3,5-trimethylcyclohexenyl ethyl ether is from about 1:1000 to about 1:15000.

9. The process of claim 7 wherein said catalyst is palladium on carbon.

10. The process of claim 8 wherein said molar ratio is from about 1:1000 to about 1:5000.

11. The process of claim 10 wherein said catalyst is palladium on carbon.

12. The process of claim 1 wherein the process is carried out in the absence of any solvent.

* * * * *